United States Patent
Siegel et al.

(10) Patent No.: US 9,682,975 B2
(45) Date of Patent: Jun. 20, 2017

(54) METHOD OF PREPARING GLUCOSYLCERAMIDE SYNTHASE INHIBITORS

(71) Applicant: Genzyme Corporation, Cambridge, MA (US)

(72) Inventors: Craig S. Siegel, Woburn, MA (US); Rayomand Gimi, Bridgewater, NJ (US); Michael Reardon, North Attleboro, MA (US); Jin Zhao, Framingham, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 14/776,443

(22) PCT Filed: Mar. 13, 2014

(86) PCT No.: PCT/US2014/025384
§ 371 (c)(1),
(2) Date: Sep. 14, 2015

(87) PCT Pub. No.: WO2014/151291
PCT Pub. Date: Sep. 25, 2014

(65) Prior Publication Data
US 2016/0039806 A1  Feb. 11, 2016

Related U.S. Application Data

(60) Provisional application No. 61/791,913, filed on Mar. 15, 2013.

(51) Int. Cl.
| | | |
|---|---|---|
| *C07D 453/00* | (2006.01) | |
| *C07D 453/02* | (2006.01) | |
| *C07D 417/06* | (2006.01) | |
| *C07D 277/30* | (2006.01) | |
| *C07D 417/12* | (2006.01) | |

(52) U.S. Cl.
CPC ......... *C07D 453/02* (2013.01); *C07D 277/30* (2013.01); *C07D 417/06* (2013.01); *C07D 417/12* (2013.01)

(58) Field of Classification Search
CPC .................................................. C07D 453/00
USPC ........................................................ 546/133
See application file for complete search history.

(56) References Cited

U.S. PATENT DOCUMENTS 9,139,580 B2 * 9/2015 Bourque .............. A61K 31/439

FOREIGN PATENT DOCUMENTS

| DE | 1768808 A1 | 1/1972 |
| DE | 4326510 A1 | 2/1995 |
| EP | 0747355 A1 | 12/1996 |
| GB | 725228 A | 3/1955 |
| WO | 9730998 A1 | 8/1997 |
| WO | 2005068426 A1 | 7/2005 |
| WO | 2006053043 A2 | 5/2006 |
| WO | 2012063933 A1 | 5/2012 |
| WO | 2012129084 A2 | 9/2012 |
| WO | 2012175119 A1 | 12/2012 |
| WO | 2014043068 A1 | 3/2014 |

OTHER PUBLICATIONS

Dube, P., et al., "Carbonyldiimidazole-mediated Lossen Rearrangement", Organic Letters, 2005, vol. 11 (24), pp. 5622-5625.
El Alwani M., et al., "Regulation of the Sphingolipid Signaling Pathways in the Growing and Hypoxic Rat Heart," Prostaglandins & Other Lipid Mediators, 2005, vol. 78 (1-4), pp. 249-263.
Geffken D., "3-(1-Hydroxyalkyl)-1,4,2-dioxazol-5-one und 3-Hydroxyoxazolidin-2,4-dione aus 2-Hydroxycarbohydroxamsäuren und 1,1'-Carbonyldiimidazol)," Liebigs Annalen der Chemie, 1982, vol. 1982 (2), pp. 211-218.
International Preliminary Report on Patentability for Application No. PCT/US2014/025384, mailed on Sep. 15, 2015, 13 pages.
International Search Report and Written Opinion for Application No. PCT/US2014/025384, mailed on Aug. 18, 2014, 20 pages.
Mazurov A., et al., "2-(Arylmethyl)-3-Substituted Quinuclidines as Selective Alpha 7 Nicotinic Receptor Ligands," Bioorganic & Medicinal Chemistry Letters, 2005, vol. 15 (8), pp. 2073-2077.
Middleton W.J., "1,3,4-Dioxazol-2-ones: a potentially hazardous class of compounds," The Journal of Organic Chemistry, 1983, vol. 48 (21), pp. 3845-3847.
Treiber A., et al., "The Pharmacokinetics and Tissue Distribution of the Glucosylceramide Synthase Inhibitor Miglustat in the Rat," Xenobiotica, vol. 37 (3), pp. 298-314.
Turzanski J., et al., "P-Glycoprotein Is Implicated in the Inhibition of Ceramide-Induced Apoptosis in Tf-1 Acute Myeloid Leukemia Cells by Modulation of the Glucosylceramide Synthase Pathwa," Experimental Hematology, 2005, 33 (1), pp. 62-72.
Yamashita T., et al., "A Vital Role for Glycosphingolipid Synthesis during Development and Differentiation," Proceedings of the National Academy of Sciences, United States of America, 1999, vol. 96 (16), pp. 9142-9147.

* cited by examiner

*Primary Examiner* — Niloofar Rahmani
(74) *Attorney, Agent, or Firm* — Peter Korakas

(57) ABSTRACT

The invention relates to a method of preparing inhibitors of glucosylceramide synthase (GCS) useful for the treatment metabolic diseases, such as lysosomal storage diseases, either alone or in combination with enzyme replacement therapy, and for the treatment of cancer.

7 Claims, No Drawings

METHOD OF PREPARING GLUCOSYLCERAMIDE SYNTHASE INHIBITORS

BACKGROUND OF THE INVENTION

The invention relates to a method of preparing inhibitors of glucosylceramide synthase (GCS) useful for the treatment metabolic diseases, such as lysosomal storage diseases, either alone or in combination with enzyme replacement therapy, and for the treatment of cancer.

Glucosylceramide synthase (GCS) is a pivotal enzyme which catalyzes the initial glycosylation step in the biosynthesis of glucosylceramide-base glycosphingolipids (GSLs) namely via the pivotal transfer of glucose from UDP-glucose (UDP-Glc) to ceramide to form glucosylceramide. GCS is a transmembrane, type III integral protein localized in the cis/medial Golgi. Glycosphingolipids (GSLs) are believed to be integral for the dynamics of many cell membrane events, including cellular interactions, signaling and trafficking. Synthesis of GSL structures has been shown (see, Yamashita et al., Proc. Natl. Acad. Sci. USA 1999, 96(16), 9142-9147) to be essential for embryonic development and for the differentiation of some t issues. Ceramide plays a central role in sphingolipid metabolism and down-regulation of GCS activity has been shown to have marked effects on the sphingolipid pattern with diminished expression of glycosphingolipids. Sphingolipids (SLs) have a biomodulatory role in physiological as well as pathological cardiovascular conditions. In particular, sphingolipids and their regulating enzymes appear to play a role in adaptive responses to chronic hypoxia in the neonatal rat heart (see, El Alwanit et al., Prostaglandins & Other Lipid Mediators 2005, 78(1-4), 249-263).

GCS inhibitors have been proposed for the treatment of a variety of diseases (see for example, WO2005068426). Such treatments include treatment of glycolipid storage diseases (e.g., Tay Sachs, Sandhoffs, GM2 Activator deficiency, GM1 gangliosidosis and Fabry diseases), diseases associated with glycolipid accumulation (e.g., Gaucher disease; Miglustat (Zavesca), a GCS inhibitor, has been approved for therapy in type 1 Gaucher disease patients, see, Treiber et al., Xenobiotica 2007, 37(3), 298-314), diseases that cause renal hypertrophy or hyperplasia such as diabetic nephropathy; diseases that cause hyperglycemia or hyperinsulemia; cancers in which glycolipid synthesis is abnormal, infectious diseases caused by organisms which use cell surface glycolipids as receptors, infectious diseases in which synthesis of glucosylceramide is essential or important, diseases in which synthesis of glucosylceramide is essential or important, diseases in which excessive glycolipid synthesis occurs (e.g., atherosclerosis, polycystic kidney disease, and renal hypertrophy), neuronal disorders, neuronal injury, inflammatory diseases or disorders associated with macrophage recruitment and activation (e.g., rheumatoid arthritis, Crohn's disease, asthma and sepsis) and diabetes mellitus and obesity (see, WO 2006053043).

In particular, it has been shown that overexpression of GCS is implicated in multi-drug resistance and disrupts ceramide-induced apoptosis. For example, Turzanski et al., (Experimental Hematology 2005, 33 (1), 62-72 have shown that ceramide induces apoptosis in acute myeloid leukemia (AML) cells and that P-glycoprotein (p-gp) confers resistance to ceramide-induced apoptosis, with modulation of the ceramide-glucosylceramide pathway making a marked contribution to this resistance in TF-1 cells. Thus, GCS inhibitors can be useful for treatment of proliferative disorders by inducing apoptosis in diseased cells.

SUMMARY OF THE INVENTION

The present invention relates to a method of preparing a compound of the formula,

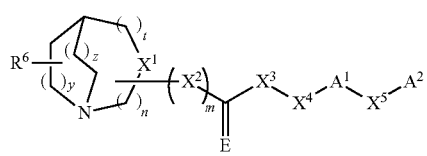

wherein:
n is 1, 2 or 3;
m is 1;
t is 0, 1 or 2;
y is 1 or 2;
z is 0, 1 or 2;
E is O;
$X^1$ is $CR^1$;
$X^2$ is O;
$X^3$ is —NH;
$X^4$ is $CR^4R^5$, $CH_2 CR^4R^5$ or $CH_2$—$(C_1$-$C_6)$ alkyl-$CR^4R^5$;
$X^5$ is a direct bond, O, S, $SO_2$, $CR^4R^5$; $(C_1$-$C_6)$alkyl, $(C_1$-$C_6)$alkyloxy, $(C_1$-$C_6)$alkenyl, $(C_1$-$C_6)$alkenyloxy;
R is $(C_6$-$C_{12})$aryl, $(C_2$-$C_9)$heteroaryl, $(C_1$-$C_6)$alkyl, $(C_2$-$C_9)$heteroaryl$(C_1$-$C_6)$alkyl;
$R^1$ is H, CN, $(C_1$-$C_6)$alkylcarbonyl, or $(C_1$-$C_6)$alkyl;
$R^2$ and $R^3$ are each independently —H, $(C_1$-$C_6)$alkyl optionally substituted by one or more substituents selected from the group consisting of halogen, $(C_1$-$C_6)$alkyl, $(C_6$-$C_{12})$aryl, $(C_2$-$C_9)$heteroaryl, $(C_1$-$C_6)$alkyl$(C_6$-$C_{12})$aryl, halo $(C_6$-$C_{12})$aryl, and halo$(C_2$-$C_9)$heteroaryl, or optionally when $X^2$ is —$NR^2$ and $X^3$ is —$NR^3$, $R^2$ and $R^3$ may be taken together with the nitrogen atoms to which they are attached form a non-aromatic heterocyclic ring optionally substituted by with one or more substituents selected from halogen, $(C_1$-$C_6)$alkyl, $(C_6$-$C_{12})$aryl, $(C_2$-$C_9)$heteroaryl, $(C_1$-$C_6)$alkyl $(C_6$-$C_{12})$aryl, halo$(C_6$-$C_{12})$aryl, and halo$(C_2$-$C_9)$heteroaryl;
$R^4$ and $R^5$ are independently selected from H, $(C_1$-$C_6)$ alkyl, or taken together with the carbon to which they are attached to form a spiro $(C_3$-$C_{10})$cycloalkyl ring or spiro $(C_3$-$C_{10})$cycloalkoxy ring;
$R^6$ is —H, halogen, —CN, $(C_6$-$C_{12})$aryl, $(C_6$-$C_{12})$aryloxy, $(C_1$-$C_6)$alkyloxy; $(C_1$-$C_6)$alkyl optionally substituted by one to four halo or $(C_1$-$C_6)$alkyl;
$A^1$ is $(C_2$-$C_6)$alkynyl; $(C_3$-$C_{10})$cycloalkyl, $(C_6$-$C_{12})$aryl, $(C_2$-$C_9)$heteroaryl, $(C_2$-$C_9)$heterocycloalkyl or benzo$(C_2$-$C_9)$heterocycloalkyl optionally substituted with one or more substituents selected from the group consisting of halo, $(C_1$-$C_6)$alkyl optionally substituted by one to three halo; $(C_1$-$C_6)$alkenyl, amino, $(C_1$-$C_6)$alkylamino, $(C_1$-$C_6)$dialkylamino, $(C_1$-$C_6)$alkoxy, nitro, CN, —OH, $(C_1$-$C_6)$alkyloxy optionally substituted by one to three halo; $(C_1$-$C_6)$alkoxycarbonyl, and $(C_1$-$C_6)$ alkylcarbonyl;
$A^2$ is H, $(C_3$-$C_{10})$cycloalkyl, $(C_6$-$C_{12})$aryl, $(C_2$-$C_9)$heteroaryl, $(C_2$-$C_9)$heterocycloalkyl or benzo$(C_2$-$C_9)$heterocycloalkyl optionally substituted with one or more substituents selected from the group consisting of halo, $(C_1$-$C_6)$alkyl optionally substituted by one to three halo; $(C_1$-$C_6)$alkylenyl, amino, $(C_1$-$C_6)$ alkylamino, $(C_1$-$C_6)$dialkylamino, $(C_1$-$C_6)$alkoxy, O(C3-C6 cycloalkyl), $(C_3$-$C_6)$ cycloalkoxy, nitro, CN, OH, $(C_1$-$C_6)$alkyloxy optionally substituted by one to three halo; $(C_3$-$C_6)$ cycloalkyl, $(C_1$-$C_6)$ alkoxycarbonyl, $(C_1$-$C_6)$ alkylcarbonyl, $(C_1$-$C_6)$ haloalkyl;

with the proviso that the sum of n+t+y+z is not greater than 6; comprising reacting the compound of Formula II

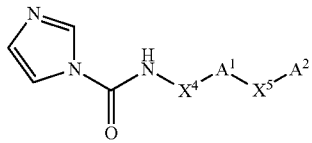

with the compound of Formula III

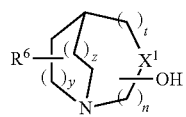

wherein n, t, y, z, $X^4$, $A^1$, $X^5$ and $A^2$ are as defined above.

The present invention relates to a method of preparing a compound of the formula,

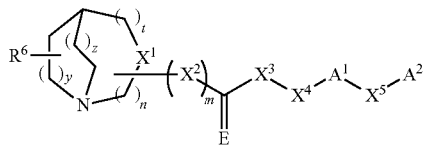

wherein:
n is 1, 2 or 3;
m is 1;
t is 0, 1 or 2;
y is 1 or 2;
z is 0, 1 or 2;
E is O;
$X^1$ is $CR^1$;
$X^2$ is O;
$X^3$ is —NH;
$X^4$ is $CR^4R^5$, $CH_2$ $CR^4R^5$ or $CH_2$—$(C_1$-$C_6)$ alkyl-$CR^4R^5$;
$X^5$ is a direct bond, O, S, $SO_2$, $CR^4R^5$; $(C_1$-$C_6)$alkyl, $(C_1$-$C_6)$alkyloxy, $(C_1$-$C_6)$alkenyl, $(C_1$-$C_6)$alkenyloxy;
R is $(C_6$-$C_{12})$aryl, $(C_2$-$C_9)$heteroaryl, $(C_1$-$C_6)$alkyl, $(C_2$-$C_9)$heteroaryl$(C_1$-$C_6)$alkyl;
$R^1$ is H, CN, $(C_1$-$C_6)$alkylcarbonyl, or $(C_1$-$C_6)$alkyl;
$R^2$ and $R^3$ are each independently —H, $(C_1$-$C_6)$alkyl optionally substituted by one or more substituents selected from the group consisting of halogen, $(C_1$-$C_6)$alkyl, $(C_6$-$C_{12})$aryl, $(C_2$-$C_9)$heteroaryl, $(C_1$-$C_6)$alkyl$(C_6$-$C_{12})$aryl, halo$(C_6$-$C_{12})$aryl, and halo$(C_2$-$C_9)$heteroaryl, or optionally when $X^2$ is —$NR^2$ and $X^3$ is —$NR^3$, $R^2$ and $R^3$ may be taken together with the nitrogen atoms to which they are attached form a non-aromatic heterocyclic ring optionally substituted by with one or more substituents selected from halogen, $(C_1$-$C_6)$alkyl, $(C_6$-$C_{12})$aryl, $(C_2$-$C_9)$heteroaryl, $(C_1$-$C_6)$alkyl $(C_6$-$C_{12})$aryl, halo$(C_6$-$C_{12})$aryl, and halo$(C_2$-$C_9)$heteroaryl;
$R^4$ and $R^5$ are independently selected from H, $(C_1$-$C_6)$ alkyl, or taken together with the carbon to which they are attached to form a spiro $(C_3$-$C_{10})$cycloalkyl ring or spiro $(C_3$-$C_{10})$cycloalkoxy ring;

$R^6$ is —H, halogen, —CN, $(C_6$-$C_{12})$aryl, $(C_6$-$C_{12})$aryloxy, $(C_1$-$C_6)$alkyloxy; $(C_1$-$C_6)$alkyl optionally substituted by one to four halo or $(C_1$-$C_6)$alkyl;
$A^1$ is $(C_2$-$C_6)$alkynyl; $(C_3$-$C_{10})$cycloalkyl, $(C_6$-$C_{12})$aryl, $(C_2$-$C_9)$heteroaryl, $(C_2$-$C_9)$heterocycloalkyl or benzo$(C_2$-$C_9)$heterocycloalkyl optionally substituted with one or more substituents selected from the group consisting of halo, $(C_1$-$C_6)$alkyl optionally substituted by one to three halo; $(C_1$-$C_6)$alkenyl, amino, $(C_1$-$C_6)$alkylamino, $(C_1$-$C_6)$dialkylamino, $(C_1$-$C_6)$alkoxy, nitro, CN, —OH, $(C_1$-$C_6)$alkyloxy optionally substituted by one to three halo; $(C_1$-$C_6)$alkoxycarbonyl, and $(C_1$-$C_6)$ alkylcarbonyl;
$A^2$ is H, $(C_3$-$C_{10})$cycloalkyl, $(C_6$-$C_{12})$aryl, $(C_2$-$C_9)$heteroaryl, $(C_2$-$C_9)$heterocycloalkyl or benzo$(C_2$-$C_9)$heterocycloalkyl optionally substituted with one or more substituents selected from the group consisting of halo, $(C_1$-$C_6)$alkyl optionally substituted by one to three halo; $(C_1$-$C_6)$alkylenyl, amino, $(C_1$-$C_6)$ alkylamino, $(C_1$-$C_6)$dialkylamino, $(C_1$-$C_6)$alkoxy, O(C3-C6 cycloalkyl), $(C_3$-$C_6)$ cycloalkoxy, nitro, CN, OH, $(C_1$-$C_6)$alkyloxy optionally substituted by one to three halo; $(C_3$-$C_6)$ cycloalkyl, $(C_1$-$C_6)$ alkoxycarbonyl, $(C_1$-$C_6)$ alkylcarbonyl, $(C_1$-$C_6)$ haloalkyl;

with the proviso that the sum of n+t+y+z is not greater than 6; comprising reacting the compound of Formula IV

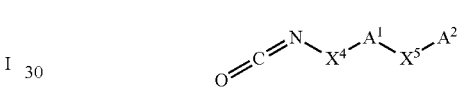

with a compound of Formula III

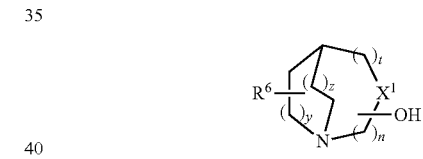

wherein n, t, y, z, $X^4$, $A^1$, $X^5$ and $A^2$ are as defined above.

The present invention relates to a method of preparing a compound of the formula,

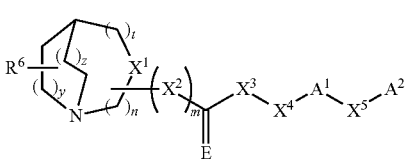

wherein:
n is 1, 2 or 3;
m is 1;
t is 0, 1 or 2;
y is 1 or 2;
z is 0, 1 or 2;
E is O;
$X^1$ is $CR^1$;
$X^2$ is O;
$X^3$ is —NH;
$X^4$ is $CR^4R^5$, $CH_2$ $CR^4R^5$ or $CH_2$—$(C_1$-$C_6)$ alkyl-$CR^4R^5$;
$X^5$ is a direct bond, O, S, $SO_2$, $CR^4R^5$; $(C_1$-$C_6)$alkyl, $(C_1$-$C_6)$alkyloxy, $(C_1$-$C_6)$alkenyl, $(C_1$-$C_6)$alkenyloxy;

R is $(C_6-C_{12})$aryl, $(C_2-C_9)$heteroaryl, $(C_1-C_6)$alkyl, $(C_2-C_9)$heteroaryl$(C_1-C_6)$alkyl;

$R^1$ is H, CN, $(C_1-C_6)$alkylcarbonyl, or $(C_1-C_6)$alkyl;

$R^2$ and $R^3$ are each independently —H, $(C_1-C_6)$alkyl optionally substituted by one or more substituents selected from the group consisting of halogen, $(C_1-C_6)$alkyl, $(C_6-C_{12})$aryl, $(C_2-C_9)$heteroaryl, $(C_1-C_6)$alkyl$(C_6-C_{12})$aryl, halo$(C_6-C_{12})$aryl, and halo$(C_2-C_9)$heteroaryl, or optionally when $X^2$ is —$NR^2$ and $X^3$ is —$NR^3$, $R^2$ and $R^3$ may be taken together with the nitrogen atoms to which they are attached form a non-aromatic heterocyclic ring optionally substituted by with one or more substituents selected from halogen, $(C_1-C_6)$alkyl, $(C_6-C_{12})$aryl, $(C_2-C_9)$heteroaryl, $(C_1-C_6)$alkyl $(C_6-C_{12})$aryl, halo$(C_6-C_{12})$aryl, and halo$(C_2-C_9)$heteroaryl;

$R^4$ and $R^5$ are independently selected from H, $(C_1-C_6)$ alkyl, or taken together with the carbon to which they are attached to form a spiro $(C_3-C_{10})$cycloalkyl ring or spiro $(C_3-C_{10})$cycloalkoxy ring;

$R^6$ is —H, halogen, —CN, $(C_6-C_{12})$aryl, $(C_6-C_{12})$aryloxy, $(C_1-C_6)$alkyloxy; $(C_1-C_6)$alkyl optionally substituted by one to four halo or $(C_1-C_6)$alkyl;

$A^1$ is $(C_2-C_6)$alkynyl; $(C_3-C_{10})$cycloalkyl, $(C_6-C_{12})$aryl, $(C_2-C_9)$heteroaryl, $(C_2-C_9)$heterocycloalkyl or benzo$(C_2-C_9)$heterocycloalkyl optionally substituted with one or more substituents selected from the group consisting of halo, $(C_1-C_6)$alkyl optionally substituted by one to three halo; $(C_1-C_6)$alkenyl, amino, $(C_1-C_6)$alkylamino, $(C_1-C_6)$dialkylamino, $(C_1-C_6)$alkoxy, nitro, CN, —OH, $(C_1-C_6)$alkyloxy optionally substituted by one to three halo; $(C_1-C_6)$alkoxycarbonyl, and $(C_1-C_6)$ alkylcarbonyl;

$A^2$ is H, $(C_3-C_{10})$cycloalkyl, $(C_6-C_{12})$aryl, $(C_2-C_9)$heteroaryl, $(C_2-C_9)$heterocycloalkyl or benzo$(C_2-C_9)$heterocycloalkyl optionally substituted with one or substituents selected from the group consisting of halo, $(C_1-C_6)$alkyl optionally substituted by one to three halo; $(C_1-C_6)$alkylenyl, amino, $(C_1-C_6)$ alkylamino, $(C_1-C_6)$dialkylamino, $(C_1-C_6)$alkoxy, O(C3-C6 cycloalkyl), $(C_3-C_6)$ cycloalkoxy, nitro, CN, OH, $(C_1-C_6)$alkyloxy optionally substituted by one to three halo; $(C_3-C_6)$ cycloalkyl, $(C_1-C_6)$ alkoxycarbonyl, $(C_1-C_6)$ alkylcarbonyl, $(C_1-C_6)$ haloalkyl;

with the proviso that the sum of n+t+y+z is not greater than 6; comprising reacting the compounds of Formula II and Formula IV

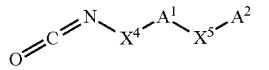

II with a compound of Formula III

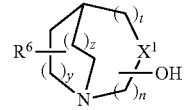

III wherein n, t, y, z, $X^4$, $A^1$, $X^5$ and $A^2$ are as defined above.

The present invention further relates to a method wherein n is 1; t is 0; y is 1 and z is 1.

The present invention further relates to a method wherein $X^4$ is $CR^4R^5$.

The present invention further relates to a method wherein $R^4$ and $R^5$ are each methyl.

The present invention further relates to a method wherein $A^1$ is $(C_2-C_9)$heteroaryl.

The present invention further relates to a method wherein $A^1$ is thiophene, thiazole, isothiazole, furane, oxazole, isoxazole, pyrrole, imidazole, pyrazole, triazole, pyridine, pymiridine, pyridazine, indole, benzotiazole, benzoisoxazole, benzopyrazole, benzoimidazole, benzofuran, benzooxazole or benzoisoxazole.

The present invention further relates to a method wherein $A^1$ is thiazole.

The present invention further relates to a method wherein $R^6$ is H.

The present invention further relates to a method wherein $X^5$ is a direct bond.

The present invention further relates to a method wherein $A^2$ is $(C_6-C_{12})$aryl.

The present invention further relates to a method wherein $A^2$ is phenyl.

The present invention further relates to a method wherein the phenyl group is substituted by halo.

The present invention further relates to a method wherein the halo group is fluoro.

The present invention further relates to a method wherein $R^1$ is hydrogen.

The present invention further relates to a method including reacting the compound of Formula V

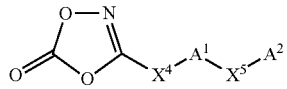

V with imidazole to form the compound of Formula II

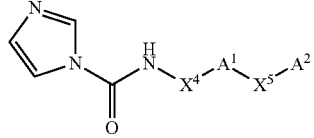

II wherein $X^4$, $A^1$, $X^5$ and $A^2$ are as defined above.

The present invention further relates to a method including heating to reflux the compound of Formula V

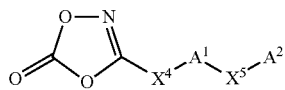

V to form the compound of Formula IV

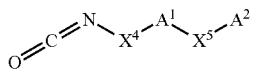

IV wherein $X^4$, $A^1$, $X^5$ and $A^2$ are as defined above.

The present invention further relates to a method including reacting, while heating to reflux, the compound of Formula V

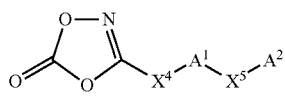

V with imidazole to form the compounds of Formula II and Formula IV

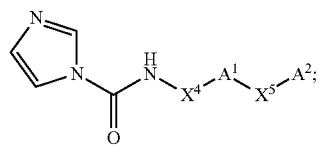

II

IV wherein $X^4$, $A^1$, $X^5$ and $A^2$ are as defined above.

The present invention further relates to a method including reacting the compound of Formula VI

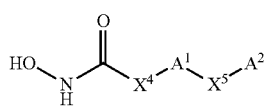

VI with N,N'-carbonyldiimidazole to form the compound of Formula V

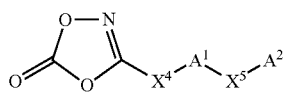

V wherein $X^4$, $A^1$, $X^5$ and $A^2$ are as defined above.

The present invention further relates to a method including reacting the compound of Formula VII

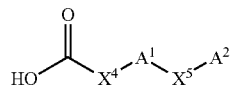

VII with N,N'-carbonyldiimidazole and hydroxylamine to form the compound of Formula VI

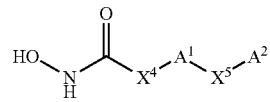

VI wherein $X^4$, $A^1$, $X^5$ and $A^2$ are as defined above.

The present invention relates to a method of preparing the compound of Formula VIII

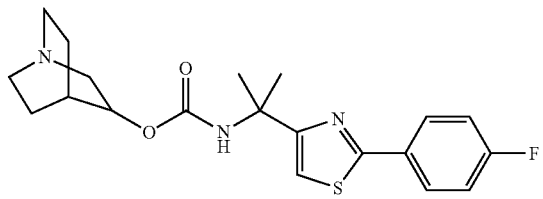

VIII comprising reacting a compound of Formula IX

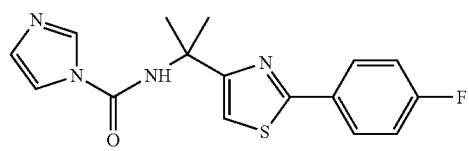

IX with quinuclidinol.

The present invention relates to a method of preparing the compound of Formula VIII

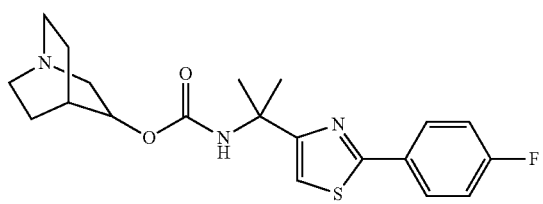

VIII comprising reacting a compound of Formula X

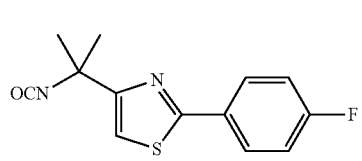

with quinuclidinol.

The present invention relates to a method of preparing the compound of Formula VIII

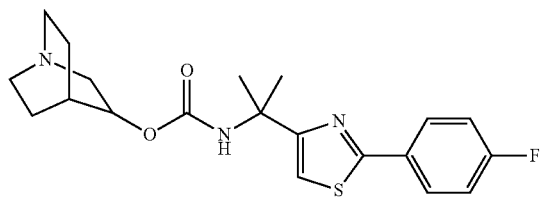

comprising reacting a compounds of Formula IX and Formula X

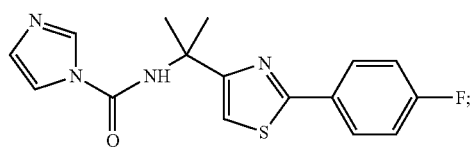

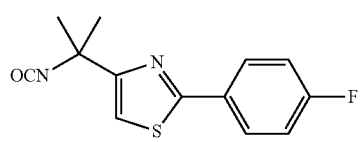

with quinuclidinol.

The present invention further relates to a method including reacting the compound of Formula XI

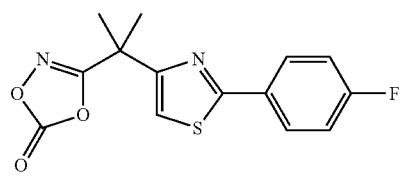

with imidazole to form the compound of Formula IX

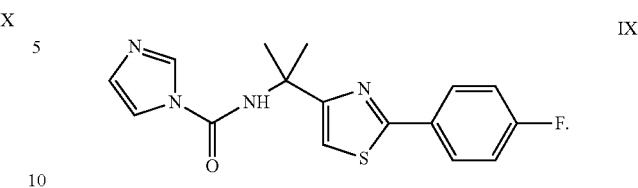

The present invention further relates to a method including heating to reflux the compound of Formula XI

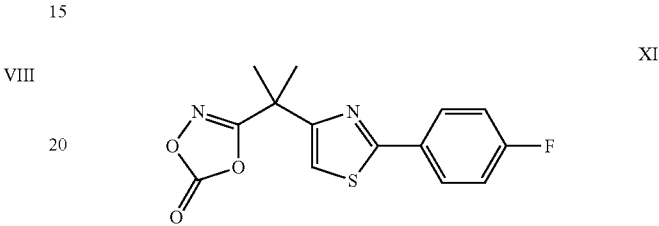

to form the compound of Formula X

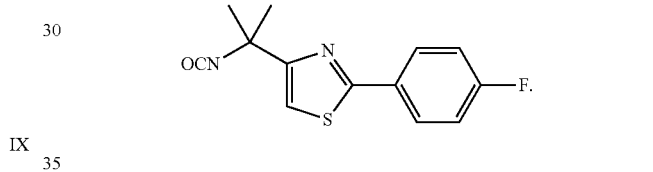

The present invention further relates to a method including reacting, while heating to reflux, the compound of Formula XI

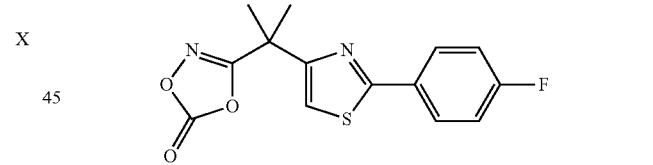

with imidazole to form the compounds of Formula IX and Formula X

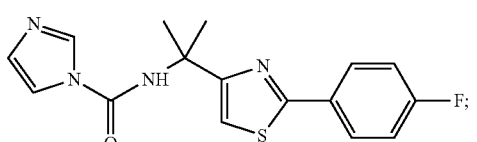

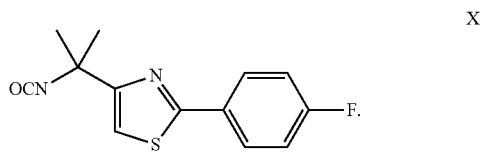

The present invention further relates to a method including reacting the compound of Formula XII

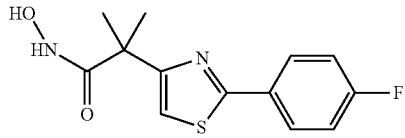

XII with N,N'-carbonyldiimidazole to form the compound of Formula XI

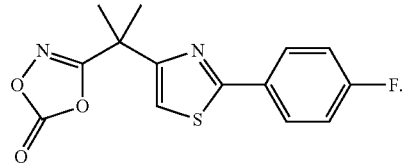

XI

The present invention further relates to a method including reacting the compound of Formula XIII

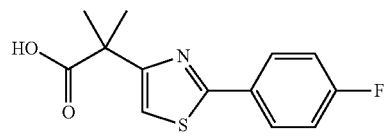

XIII with N,N'-carbonyldiimidazole and hydroxylamine to form the compound of Formula XII

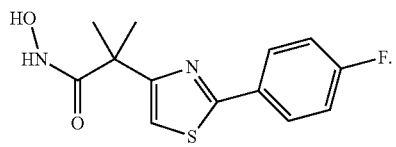

XII

The present invention further relates to a method including reacting the compound of Formula XIV

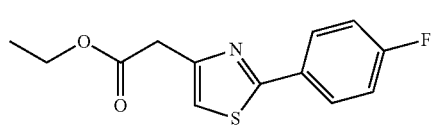

XIV with potassium tert-butoxide and methyl iodine followed by reacting the ethyl ester so formed with lithium hydroxide to form the compound of Formula XIII

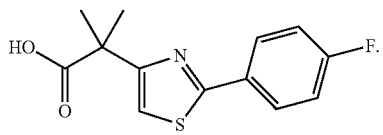

XIII

The present invention relates to a compound of Formula XII

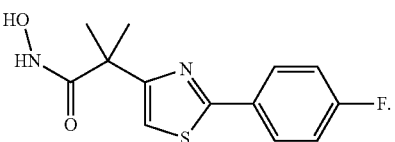

XII

The present invention relates to a compound of Formula XI

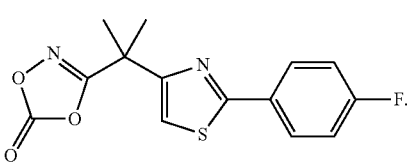

XI

The present invention relates to a compound of Formula IX

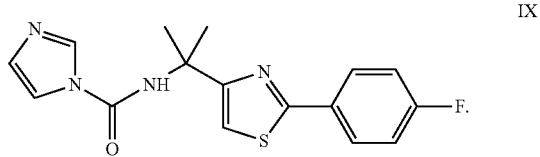 [SMILES: CC(C)(NC(=O)n1ccnc1)c1csc(-c2ccc(F)cc2)n1]

IX

DETAILED DESCRIPTION OF THE INVENTION

Scheme 1

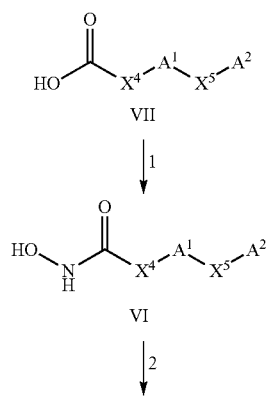

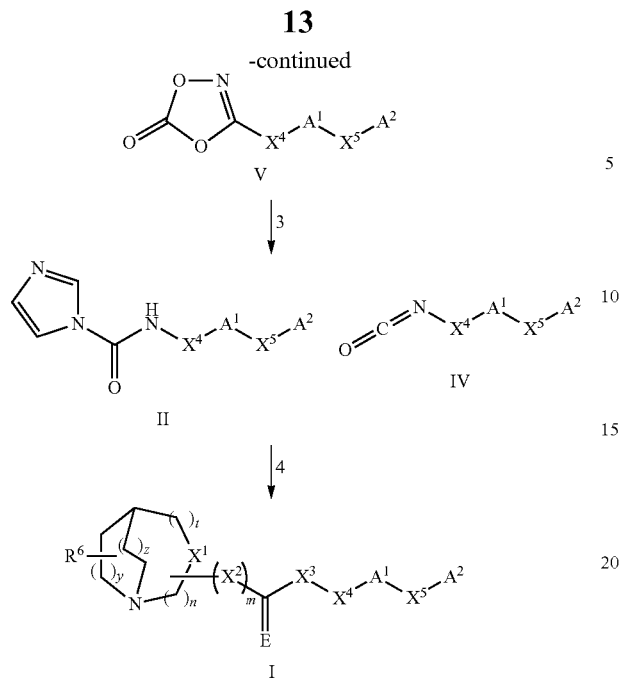

In reaction 1 of Scheme 1, the carboxylic acid compound of Formula VII is converted to the corresponding hydroxamic acid compound of Formula VI by reacting VII with N,N'-carbonyldiimidazole (i.e. CDI) in a polar aprotic solvent, such as tetrahydrofuran (THF). The solution is stirred at a temperature between about −5° C. to about 25° C., preferable about 20° C., for a time period between about 5 minutes to about 30 minutes, preferably about 10 to 15 minutes. The resulting solution mixture is allowed to warm to room temperature and stirred for an additional time period between about 30 minutes to about 2 hours, preferably about 1 hour. Hydroxylamine is then added to the solution mixture at a temperature between about −5° C. to about 10° C., preferable about 3° C. The resulting reaction mixture is stirred under inert atmosphere (i.e., nitrogen) for a time period between about 5 min to about 8 hours, preferably about 10 min.

In reaction 2 of Scheme 1, the hydroxamic acid compound of Formula VI is converted to the corresponding compound of Formula V by the addition of N,N'-carbonyldiimidazole to a solution of VI in toluene under inert atmosphere (i.e., nitrogen) and stirred for a time period between about 30 minutes to about 4 hours, preferably about 2.5 hours.

In reaction 3 of Scheme 1, the compound of Formula V is converted to the corresponding compounds of Formula II and Formula IV by reacting V with imidazole in the presence of a aprotic solvent, such as toluene. The reaction mixture is heated to reflux for a time period between about 4 hours to about 28 hours, preferable about 6 hours.

In reaction 4 of Scheme 1, a mixture of the compounds of Formula II and Formula IV (or each intermediate separately) is converted to the corresponding compound of Formula I by reacting II and IV with (S)-(+)-quinuclidinol in the presence of a aprotic solvent, such as toluene. The reaction mixture is heated to reflux for a time period between about 12 hours to about 24 hours, preferable about 18 hours.

Preparation A

To 4-Fluorophenylthioamide (50.35 g, 1 eq.) was added 8.6 weight volumes of 200 proof ethanol (based on thioamide) (430 mL) and ethyl 4-chloroacetoacetate (68.2 g, 1.1 eq.). The mixture was place under a nitrogen atmosphere. It was heated under reflux for 5 h and allowed to cool to room temperature. The solution was concentrated to an oil and TBME (10 volumes, 500 mL) and 6 volumes of saturated NaHCO3 (300 mL) added. The aqueous layer was back extracted with 5 volumes (250 mL) of TBME. The combined organic layer was washed with water and then concentrated to an oil and then dried to a solid. The product was crystallized from 3 weight volumes of hot hexanes. Yield 89% Product 98.7% pure by HPLC (area %).

Example 1

(S)-Quinuclidin-3-yl (2-(2-(4-fluorophenyl)thiazol-4-yl)propan-2-yl)carbamate

Step 1: Dimethylation with methyl iodide

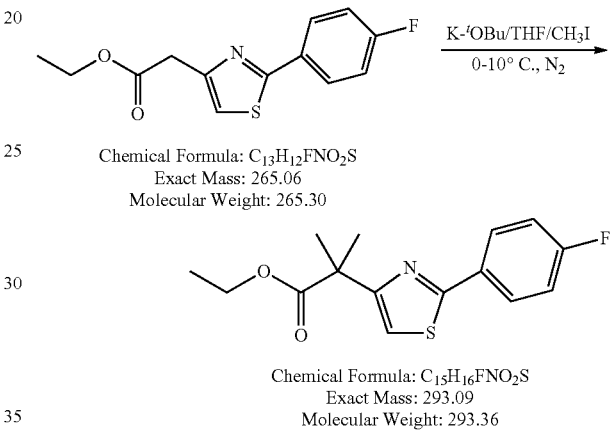

Procedure: In a 100 L reactor was added tetrahydrofuran (THF, 28.4 Kg) and potassium tert-butoxide (MW 112.21, 2.28 Kg g, 4.0 equiv.,). This mixture was cooled to 0-2° C. (internal temperature). The starting ester (MW 265.3, 2.0 Kg, 1.0 equiv.) was dissolved in THF (4 L) and transferred to the reactor over a period of 10-60 min, keeping the internal temperature below 10° C. during the addition. The reaction mixture was stirred at 3-9° C. for 15-60 min. A solution of methyl iodide (MW 141.94, 1.88 L, 4.0 equiv.) in THF (4.8 L) was added to the reactor over 30-120 min keeping the internal temperature below 10° C. A solution of NaCl (2.0 Kg) in water (14 L) was added over 10 min and the mixture was stirred for at least 10 min more. The reaction was made acidic by the addition of 1 M HCl (~1.44 L). The layers were separated and the aqueous layer was back extracted with THF (6.2 kg). The combined organic layers were vacuum distilled to ~16 l. This THF solution of the Step 1 product was used in the next reaction.

Step 2: Hydrolysis of the ethyl ester with LiOH monohydrate

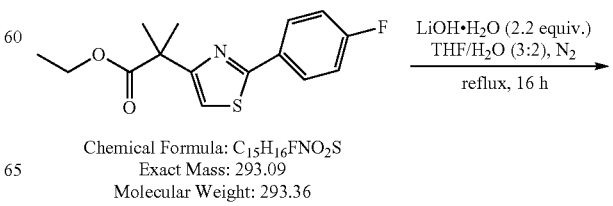

-continued

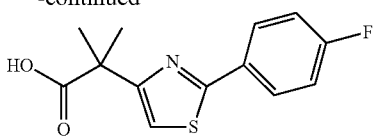

Chemical Formula: C$_{13}$H$_{12}$FNO$_2$S
Exact Mass: 265.06
Molecular Weight: 265.30

Procedure: To the ester in THF was added a solution of LiOH.H$_2$O (MW 41.96, 0.695 Kg, 2.2 equiv.) in water (9.3 L) was added. The mixture was heated at reflux for 8-16 hours. After the reactions was judge complete by HPLC, water (12 L) was added and the mixture was vacuum distilled to ~16 L. TBME (5.9 kg) was added and after stirring the layers were separated. The aqueous layer containing the product was washed a second time with TBME (5.9 Kg). TBME was added to the aqueous layer and the mixture was made acidic (pH≤3) by the addition of 5 M HCl (3.67 Kg). The layers were separated and the aqueous layer was extracted a second time with TBME (4.5 Kg). Heptane (15 Kg) was added to the combined organic layers and the mixture was vacuum distilled to ~16 L. After heating and cooling to 5-25° C. and stirring for at least 3 h, the product was filtered, washed with heptane, and vacuum dried. Yield 85.8% (2.15 Kg) HPLC purity (area %) 99.72%

Reaction 1: Formation of Hydroxamic Acid with NH$_2$OH

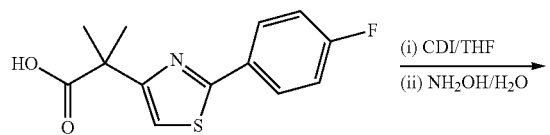

Chemical Formula: C$_{13}$H$_{12}$FNO$_2$S
Exact Mass: 265.0573
Molecular Weight: 265.3033

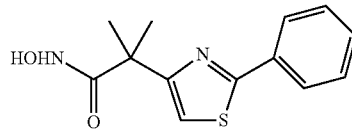

Chemical Formula: C$_{13}$H$_{13}$FN$_2$O$_2$S
Exact Mass: 280.07
Molecular Weight: 280.32

Procedure: To a 100 L reactor was added THF (14.2 Kg) and N,N'-carbonyldiimidazole (CDI; MW 162.15, 1.34 Kg, 1.1 equiv.). The acid from reaction 2 (2.0 Kg, 1.0 equiv) dissolved in THF (4 L) was added over 15-20 min. The mixture was stirred at room temperature for 2.5-3 h. The reaction was cooled to 0-3° C. Aqueous hydroxylamine (50% aqueous; 1.7 L, 4.0 equiv.) was added over 5-15 min keeping the internal temperature less than 18° C. After the addition was complete, the layers were separated and the organic layer was washed with water (12 Kg) and a solution of sodium chloride (2.0 Kg) in water (12 L). The separated organic layer was vacuum distill to ~16 l. Toluene (13.8 Kg) was added and the mixture was again vacuum distilled to ~16 L. Heptane (11 kg) was added and the mixture was stirred at room temperature for at least 16 h. The resulting solid was filtered, washed with heptane (11 Kg) and vacuum dried at room temperature. The yield was 1.58 Kg (74.8%).

Reaction 2: Conversion of Hydroxamic Acid to a Dioxazolone

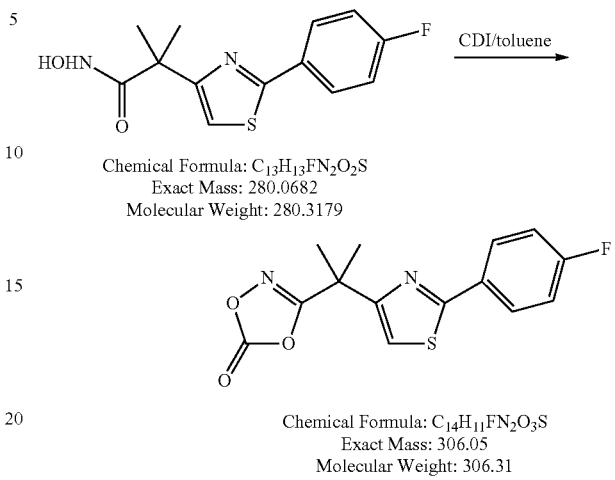

Chemical Formula: C$_{13}$H$_{13}$FN$_2$O$_2$S
Exact Mass: 280.0682
Molecular Weight: 280.3179

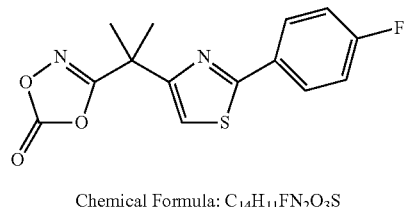

Chemical Formula: C$_{14}$H$_{11}$FN$_2$O$_3$S
Exact Mass: 306.05
Molecular Weight: 306.31

Procedure: Toluene (17.3 Kg) and the hydroxamic acid from, reaction 1 (MW 280.32, 2.0 Kg) was transferred to a 100 L reactor. After stirring at room temperature for at least 15 min carbonyl diimidazole CDI (MW 162.15, 1.27 Kg, 1.1 equiv.) was added. The mixture was stirred at room temperature for 1-4 h until the reaction was judge complete by HPLC.

Reaction 3 Conversion of the Dioxazolone to a Mixture of the Imidazole Urea and Isocyanate

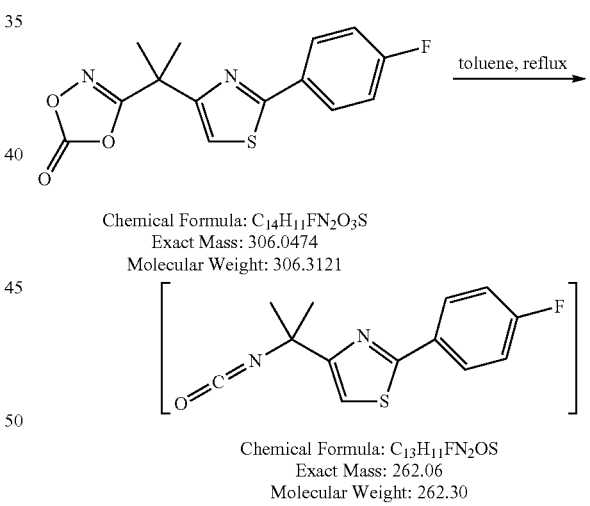

Chemical Formula: C$_{14}$H$_{11}$FN$_2$O$_3$S
Exact Mass: 306.0474
Molecular Weight: 306.3121

Chemical Formula: C$_{13}$H$_{11}$FN$_2$OS
Exact Mass: 262.06
Molecular Weight: 262.30

+

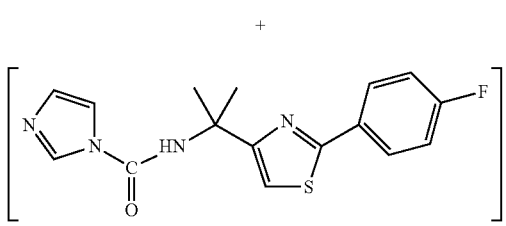

Chemical Formula: C$_{16}$H$_{15}$FN$_4$OS
Exact Mass: 330.0951
Molecular Weight: 330.3799

Procedure: The solution of the dioxazolone (reaction 2) was heated at 60° C. for 6-16 hours to complete the conversion to a mixture of the isocyanate and imidazole urea as judge by HPLC analysis.

Reaction 4: Final Conversion to the Carbamate

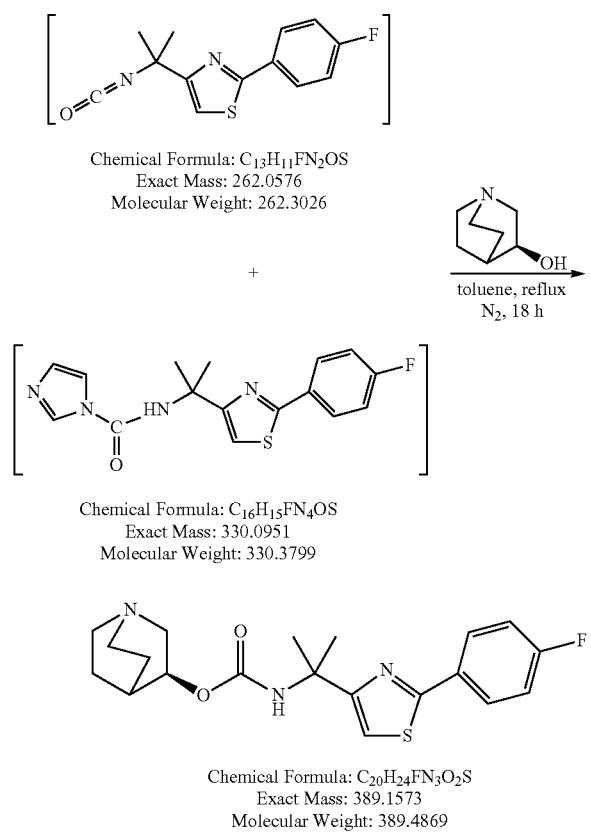

Procedure: (S)-(+)-3-quinuclidinol (1.14 Kg, 1.18 equiv.) was added to the mixture of the isocyanate and imidazole urea toluene solution (reaction 3) and the solution was heated at 100-110° C. for 18-28 h. Toluene (8.6 Kg) was added to the reaction and the mixture was washed twice with water (20 Kg). The product was removed from the organic layer with two extractions of aqueous IM HCl. (19.7 Kg). Isopropyl acetate (34.8 Kg) was added to the combined acidic aqueous layers. The mixture was cooled to 5-10° C. and 10M aqueous NaOH (5.3 Kg) was added. The layers were separated and the organic layer was vacuum distilled to ~16 L. Heptane (21.4 Kg) was added to the remaining isopropyl acetate solution and again the solution was distilled to 16 L. the resulting suspension was stirred for at least 4 h. The product was filtered, washed with heptane (13.7 Kg) and vacuum dried at room temperature. The yield was 2.3 Kg (82.8% yield). HPLC purity (Area %) 99.7%.

1H NMR (400 MHz, CDCl$_3$) δ 8.04-7.83 (m, 2H), 7.20-6.99 (m, 3H), 5.53 (s, 1H), 4.73-4.55 (m, 1H), 3.18 (dd, J=14.5, 8.4 Hz, 1H), 3.05-2.19 (m, 5H), 2.0-1.76 (m, 11H). $^{13}$C NMR (100 MHz, CDCl$_3$) δ 166.38, 165.02, 162.54, 162.8-155.0 (d, C-F), 130.06, 128.43, 128.34, 116.01, 115.79, 112.46, 71.18, 55.70, 54.13, 47.42, 46.52, 27.94, 25.41, 24.67, 19.58.

Example 2

(S)-Ouinuclidin-3-yl (2-(2-(4-fluorophenyl)thiazol-4-yl)propan-2-yl)carbamate

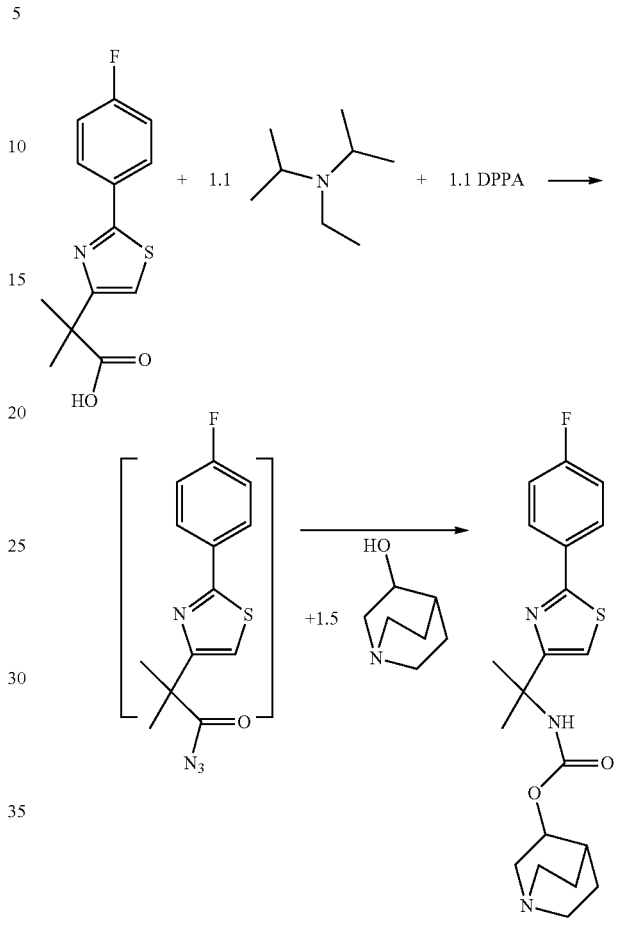

2-(2-(4-fluorophenyl)thiazol-4-yl)-2-methylpropanoic acid (1 g) and diisopropylethyl amine (0.57 ml) were dissolved in toluene and stirred at 110° C. under N2. DPPA (0.9 ml) was added dropwise. The mixture was stirred for 3 hours at 110° C. to complete the conversion of the acetyl azide and isocyanate. Quinuclidin-3-ol (0.72 g) was added and stirred for 18 hours. The result mixture was diluted with toluene (50 ml) and washed with saturated sodium bicarbonate solution. The organic layer was concentrated to oil. Product of quinuclidin-3-yl (2-(2-(4-fluorophenyl)thiazol-4-yl)propan-2-yl)carbamate was purified by crystallization from EtOAc (0.6 g).

The invention claimed is:
1. A method of preparing the compound of Formula VIII

VIII

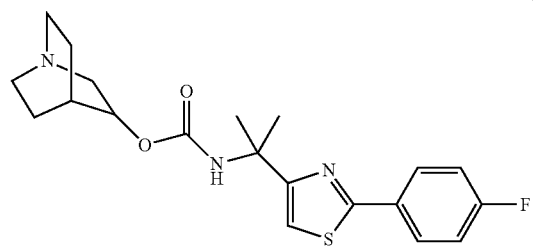

comprising reacting compounds of Formula IX and Formula X

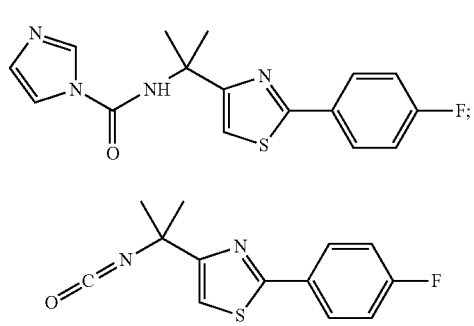

with quinuclidinol.

2. A method according to claim 1, further including reacting the compound of Formula XI

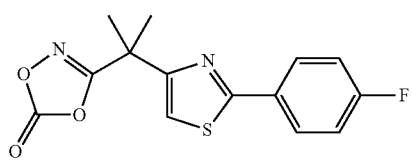

with imidazole to form the compound of Formula IX

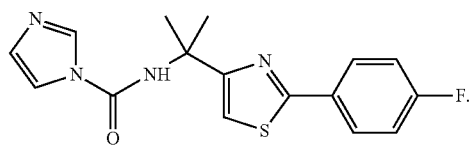

3. A method according to claim 1, further including heating to reflux the compound of Formula XI

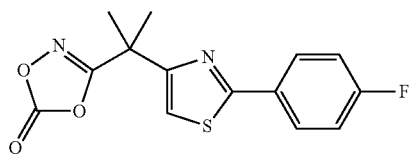

to form the compound of Formula X

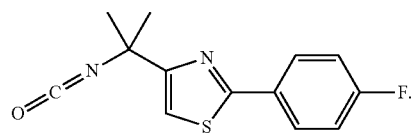

4. A method according to claim 1, further including reacting, while heating to reflux, the compound of Formula XI

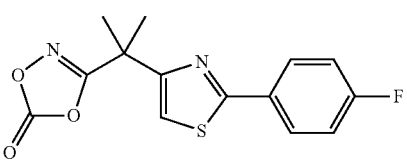

with imidazole to form the compounds of Formula IX and Formula X

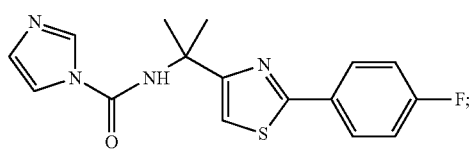

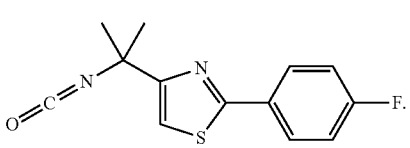

5. A method according to claim 4, further including reacting the compound of Formula XII

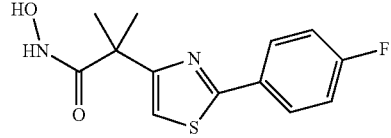

with N,N'- carbonyldiimidazole to form the compound of Formula XI

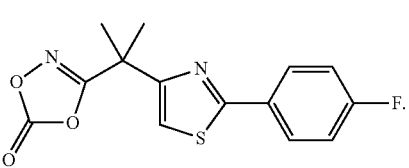

6. A method according to claim 5, further including reacting the compound of Formula XIII

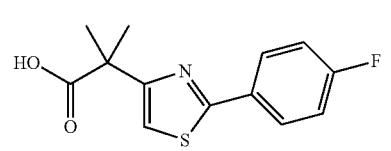

with N, N'- carbonyldiimidazole and hydroxylamine to form the compound of Formula XII
XII
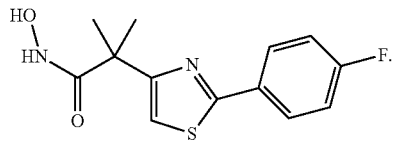
7. A method according to claim 6, further including reacting the compound of Formula XIV
XIV
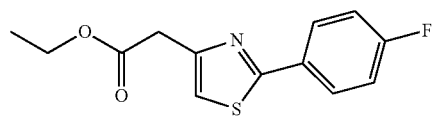
with potassium tert-butoxide and methyl iodine followed by reacting the ethyl ester so formed with lithium hydroxide to form the compound of Formula XIII
XIII
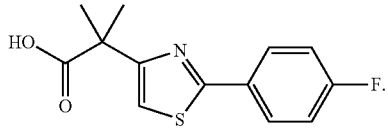
* * * * *